(12) United States Patent
Farrar

(10) Patent No.: US 7,815,685 B2
(45) Date of Patent: Oct. 19, 2010

(54) ORTHOPAEDIC JOINT PROSTHESIS

(75) Inventor: Richard Farrar, North Rigton (GB)

(73) Assignee: Depuy International Ltd. (GB)

( * ) Notice: Subject to any disclaimer, the term of this patent is extended or adjusted under 35 U.S.C. 154(b) by 467 days.

(21) Appl. No.: 10/446,681

(22) Filed: May 29, 2003

(65) Prior Publication Data

US 2005/0256584 A1 Nov. 17, 2005

(51) Int. Cl.
*A61F 2/32* (2006.01)
*A61F 2/30* (2006.01)

(52) U.S. Cl. .................... 623/22.15; 623/23.4

(58) Field of Classification Search ............ 623/17.14, 623/19.12, 20.22, 22.15, 22.17, 22.18, 22.22, 623/23.4, 23.42, 23.43

See application file for complete search history.

(56) References Cited

U.S. PATENT DOCUMENTS

| | | | | |
|---|---|---|---|---|
| 4,911,723 A | * | 3/1990 | Menschik | 623/22.15 |
| 5,156,626 A | * | 10/1992 | Broderick et al. | 623/22.12 |
| 5,383,936 A | * | 1/1995 | Kubein-Meesenburg et al. | 623/19.13 |
| 6,059,830 A | * | 5/2000 | Lippincott et al. | 623/18.11 |
| 6,610,097 B2 | * | 8/2003 | Serbousek et al. | 623/22.24 |

FOREIGN PATENT DOCUMENTS

| | | | |
|---|---|---|---|
| DE | 4428290 A1 | | 2/1996 |
| DE | 19710934 A1 | | 9/1998 |
| DE | 199 15 814 A1 | * | 10/2000 |
| DE | 19915814 A1 | | 10/2000 |
| EP | 226762 A1 | | 7/1987 |
| EP | 302850 A2 | | 2/1989 |
| EP | 1025814 A1 | | 8/2000 |
| EP | 0 748 193 B1 | * | 12/2001 |
| JP | 2002-630 A | * | 1/2002 |
| WO | WO 9523566 A1 | | 9/1995 |
| WO | WO 9716138 A1 | | 5/1997 |
| WO | WO 02/43626 A1 | * | 6/2002 |

OTHER PUBLICATIONS

Buttermilch M, et al; German Patent DE19915814, English Abstract; Dialog® File No. 351 Accession No. 10298973; Derwent World Patents Index; 2009 Derwent Information Ltd.
Kubein-Meesenburg, D., et al; German Patent DE19710934A1 English Abstract; MicroPatent Report; 2009 MicroPatent, LLC.
Kubein-Meesenburg, D., et al; German Patent DE4428290A1 English Abstract; MicroPatent Report; 2009 MicroPatent, LLC.
Muller, M.E.; European Patent EP226762A English Abstract; Dialog® File No. 351 Accession No. 4076724; Derwent World Patents Index; 2009 Derwent Information Ltd.
Menschik, A.; European Patent EP302850A2 English Abstract; ; MicroPatent Report; 2009 MicroPatent, LLC.
Cales, B. et al; European Patent EP1025814A1 English Abstract; ; MicroPatent Report; 2009 MicroPatent, LLC.

* cited by examiner

*Primary Examiner*—David H. Willse

(57) ABSTRACT

An orthopaedic joint prosthesis which is intended for the replacement of damaged or diseased joints of the human or animal body comprises a first component with a rounded head portion and a second component which comprises a hollow cup for receiving the head portion of the first component. The radius of curvature of one or both of the bearing surfaces changes varies that the bearing surface has a spherical portion at the pole and a space between the bearing surfaces which increases in size towards the lip of the cup.

14 Claims, 3 Drawing Sheets

ORTHOPAEDIC JOINT PROSTHESIS

The present invention relates to an orthopaedic joint prosthesis which is intended for the replacement of damaged or diseased ball and cup joints of the human or animal body.

Implantable joint prostheses for joints such as hip and shoulder joints comprise a rounded head on a stem which can fit into the intramedullary cavity of the long bone, and an implantable cup which can receive the rounded head for articulation of the joint.

Careful preparation of the bearing surfaces of the head and cup components of a joint prosthesis is necessary to obtain satisfactory articulation. The surfaces should have a significant contact area so that the load is spread. However, it is also important to maintain a small clearance between the bearing surfaces for lubricating fluid. Control over the clearance is important to maintain satisfactory lubrication. If the clearance is too small, it can allow direct contact between the bearing surfaces, leading to wear of the surfaces and the generation of wear debris.

Use of components which have bearing surfaces with spherical geometries requires that the diameter of the head component is slightly smaller than the internal diameter of the cup component, in order that a clearance is maintained between the surfaces. However, this means that the load is transferred between the surfaces only at a point; it is not possible to obtain a true surface-to-surface load bearing relationship when the two surfaces are spherical but with different diameters.

WO-A-97/16138 discloses a joint prosthesis in which the articulating surfaces of the head and cup components have complex configurations. Each bearing surface has a spherical portion at about its pole. The spherical portions are in surface-to-surface load bearing relationship. Each bearing surface has a non-spherical portion where the surfaces diverge, by changing the radius of curvature of the bearing surface of the cup component to a bigger value, and decreasing the radius of curvature of the bearing surface of the head component to a smaller value. The resulting bearing surfaces include line discontinuities at the point where the radii change. This can give rise to increased wear at the regions of these lines where these discontinuities are located.

WO-A-95/23566 discloses a joint prosthesis in which an acetabular cup has a concave bearing socket for receiving the head of a femoral component of a hip prosthesis. The radius of curvature of the surface of the socket continuously and monotonically decreases from the lip of the socket to a minimum value ($R_2$) at a point within the socket. The head of the ball component has a primarily spherical geometry with a radius of curvature of $R_1$, with $R_1$ being less than $R_2$ by a small amount. Away from the actual pole, the surfaces diverge to leave a increasing clearance between the monotonically diverging surfaces. The non-spherical bearing surface of this patent is continuous because the radius varies continuously and in a consistent direction (that is to say, monotonically) but decreases to a point. A problem with this design is that the disclosed bearing surfaces can never provide the load transfer characteristics which are available from two surfaces in surface to surface contact.

The present invention provides a joint prosthesis in which the radius of curvature of at least one of the joint components changes as far as a circumferential line spaced apart from the pole of the bearing surface, the portion of the bearing surface between the line and the pole having a substantially constant radius.

Accordingly, in one aspect, the invention provides an orthopaedic joint prosthesis which comprises a first component having a generally rounded head portion with a rounded bearing surface, and a second component which comprises a hollow cup for receiving the head portion of the first component and which has a rounded internal bearing surface, the bearing surfaces being symmetrical about respective axes of symmetry, in which:

(a) the radius of curvature of the bearing surface of the hollow cup continuously and monotonically decreases as the angle between the radius and the axis decreases in a direction towards the pole to a circumferential line, the portion of the bearing surface between the said line and the pole of the cup having a substantially constant radius, and/or (b) the radius of curvature of the bearing surface of the head portion continuously and monotonically increases as the angle between the radius and the axis decreases in a direction towards the pole to a circumferential line, the portion of the bearing surface between the said line and the pole of the cup having a substantially constant radius.

The joint of the present invention has the advantage that it can provide an area of surface to surface contact at the pole of the bearing surface, which allows smooth articulation of the joint. However, variation in the radius of curvature of the bearing surface means that likelihood of the joint locking against continued articulation, for example because of imperfections due to limitations on manufacturing techniques, is reduced.

The axis of the bearing surface is defined as a result of the rotational symmetry of the bearing surface. The pole of the bearing surface is at the end of the axis, which will generally be at about the top of the head portion or at about the deepest point within the cup. However, in some cases, the pole might be displaced from the acetabular axis (or from centre of the cup or the centre of the head portion) according to the requirements for load transfer.

The radius of curvature of the bearing surface at any point on its surface is measured from the centre of the cup or the head portion as the case might be. The centre of the cup or head portion is the centre of the sphere of which the portion of the bearing surface between the circumferential line and the pole forms a part, and the radius of curvature of the bearing surface at each other point on its surface is measured from the centre of this sphere. It will be understood that the angle between this radius of curvature (measured from the centre of the sphere of which the portion of the bearing surface between the circumferential line and the pole forms a part) and the bearing surface (represented by a tangent to it) might vary slightly from 90° at points at which there are deviations from sphericity, for example by up to about 1° or more.

The radius of curvature of the bearing surface changes as the angle between the radius and the axis of rotational symmetry of the bearing surface changes, that angle being zero when the radius extends from the sphere centre to the pole of the bearing surface (at or about the top of the head portion or the centre of the cup). When the bearing surface is that of the hollow cup, the variation in the radius of curvature will be such that the radius decreases as the angle between the radius and the axis decreases. When the bearing surface is that of the head portion, the variation in the radius of curvature will be such that the radius increases as the angle between the radius and the axis decreases. Generally, the angle between the radius and the axis at the point at which the variation in radius ceases (which will be half of the solid angle of the cone that is generated by rotation of the radius) will be at least about 10°, preferably at least about 20°, more preferably at least about 25°. Generally, the angle between the radius and the axis at the point at which the variation in radius ceases will be not more than about 80°, preferably not more than about 70°, more preferably not more than about 55°.

Generally, the bearing surface of the hollow cup will not be re-entrant so that the head portion of the other component can be inserted into the cup. Accordingly, the bearing surface would extend to a line at which the angle between the radius of curvature of the bearing surface and the axis of rotational symmetry of the bearing surface is less than 90 degrees. Preferably, the said angle is at least about 80 degrees, for example about 88 degrees.

Generally, the bearing surface of the head portion will preferably extend over more than a hemisphere. Accordingly, the bearing surface would extend to a line at which the angle between the radius of curvature of the bearing surface and the axis of rotational symmetry of the bearing surface is at least about 90°, preferably at least about 130°, for example at least about 150°.

Generally, the deviation from sphericity of the head portion or of the cup will be slight, for example so that a space is introduced around the head portion between the bearing surfaces which is not more about 1 mm wide, for example not more than about 500 µm, preferably not more than about 300 µm, especially not more than about 100 µm, for example not more than about 60 µm. The width of space will generally be at least about 15 µm, for example from about 20 µm to about 50 µm. The width of the space will generally increase gradually from the circumferential line at which the changes in radius cease in a direction away from the pole of the components. The width of the space between the components in the region in which the bearing surface has a constant radius of curvature will usually be substantially constant. The space in that region will often be less than about 10 µm, for example less than about 5 µm, and possibly as little as 2 µm or less.

The deviation from sphericity caused by the changing radius of curvature can be applied to one or both of the head portion and the hollow cup. Generally, the deviation will only be applied to one of the components while the other component will have a substantially constant radius of curvature over most, or preferably all, of its bearing surface. This has the advantage of simplifying manufacture of one of the components.

The prosthesis of the present invention has the further advantage that there is no discontinuity in the configuration of the bearing surface, notwithstanding the fact that the configuration of the bearing surface includes spherical and non-spherical portions. This can follow from the variation in radius of curvature of the bearing surface. The absence of a discontinuity means that the volume of wear debris that is generated during the period after implantation is reduced compared with prostheses of the kind disclosed in WO-A-97/16138.

Preferably, the shape of the portion of the bearing surface in which the radius of curvature changes is such that the geometry of the surface corresponds approximately to the shape of at least a part of a parabola, a hyperbola or an involute, or is substantially linear in the case of the hollow cup, when viewed in cross-section on the component's axis. When the shape of the bearing surface is linear in part, the configuration of bearing surface might in the case of an embodiment of hollow cup be compared with that of a shuttlecock, which is rounded at the base and is linear extending from the base (although of course the dimensions and relative sizes of the portions of the surface will be different).

The generation of the bearing surface as a parabola, hyperbola, involute or other geometric form has the advantage that the surface can be defined mathematically. The mathematical definition of the surface configuration allows use of the definition in computer controlled manufacturing equipment such as turning and milling equipment and the like.

It is particularly preferred that the shape of the portion of the bearing surface in which the radius of curvature changes is such that the geometry of the surface corresponds approximately to the shape of a part of an involute. An involute can provide a continuous and monotonic change in the effective radius of the bearing surface (measured as discussed above) as required in the prosthesis of the invention. It is believed that the variation in the effective radius that is provided by a bearing surface defined by an involute can provide an appropriate space between the bearing surfaces to reduce, and preferably to eliminate, locking of the joint against articulation. More information on the generation of an appropriate involute geometry (as applied to the design of gears) is available from the book "Gears" by H E Merritt, published by Sir Isaac Pitman Limited in 1955.

The prosthesis of the invention might be for example a hip joint prosthesis or a shoulder joint prosthesis. When the prosthesis is a hip joint prosthesis, the first component will generally be a femoral component and the second component an acetabular component. The prosthesis can be designed as a shoulder joint prosthesis, in which for example the first component will be a humeral component.

The first and second components can each be made from polymeric (for example high molecular weight polyethylenes), metallic (for example, cobalt chrome alloys, titanium alloys etc) and ceramic materials. When a polymeric material is used, it might be used as the liner of a cup component. However, the prosthesis of the invention lends itself to the use of hard materials which are less prone to wear, such as metallic and ceramic materials. For example, the bearing surfaces of both components might be made from metallic materials or ceramic materials. Often, it will be preferred for the materials of the bearing surfaces to be different, especially by using materials of which one is harder than the other. This enables control over the nature of wear debris that is generated in the period immediately after implantation. The components can be formed from two components, for example by the application of a surface layer of a first material onto a substrate formed from a second material. For example, a layer of a ceramic material might be provided on a metallic substrate.

The bearing surfaces will be finished so that they are smooth and substantially free of imperfections. Techniques for finishing the surfaces are known in connection with the manufacture of orthopaedic joint prosthesis components.

Techniques used for manufacture of the prosthesis of the invention can be based on techniques which are used conventionally in the manufacture of prosthesis components with spherical bearing surfaces, for example using rotating grinding and polishing heads against the component while the component is also rotating. The deviation from sphericity can be provided in the prosthesis by selective removal of material (for example by carefully controlled localised removal of material, such as by grinding) or by selective addition of material (for example by carefully controlled application of a coating such as of a ceramic material on to a metallic bearing component).

The present invention will now be described by way of example only with reference to the following drawings in which.

Figure 1:
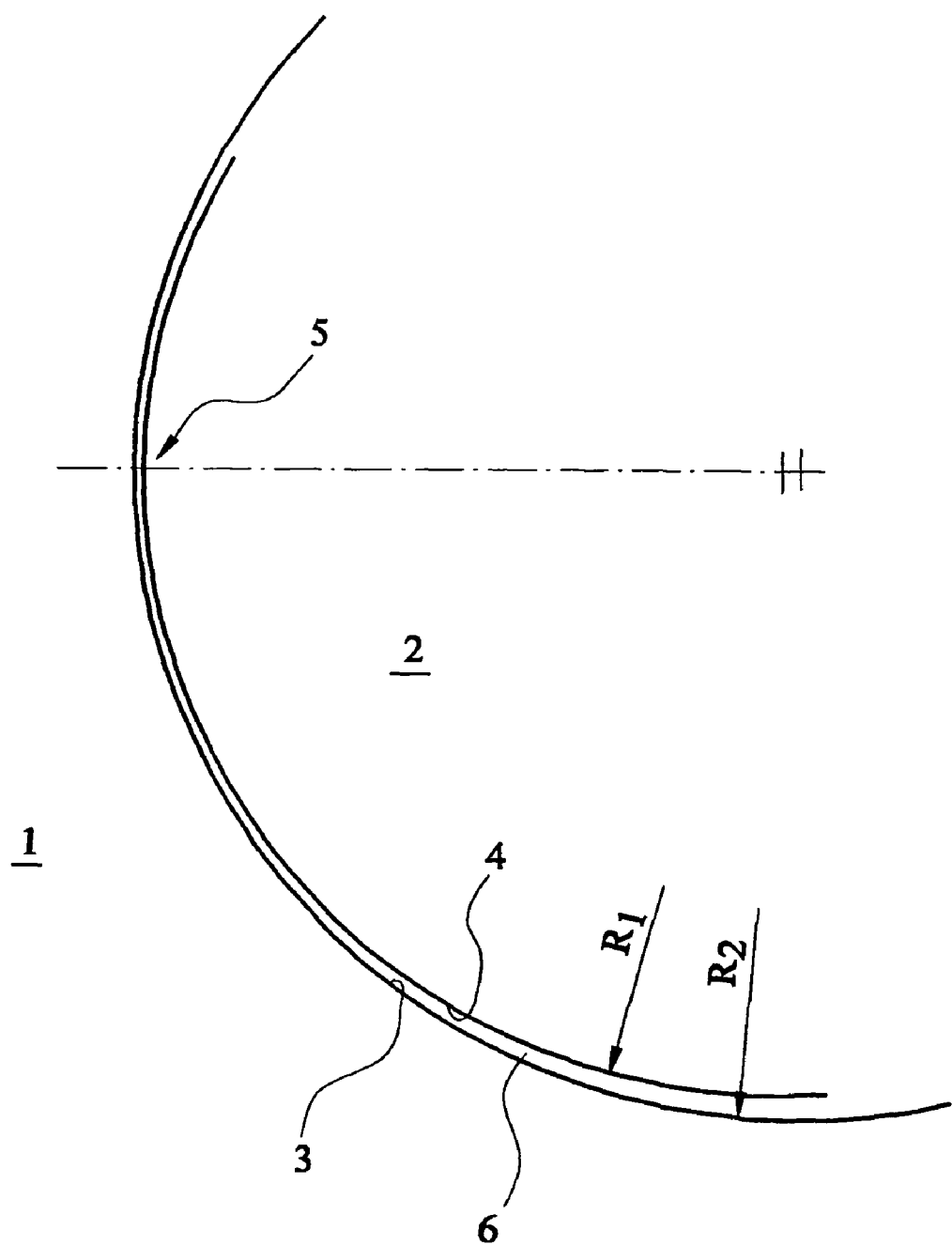
FIG. 1 illustrates a conventional sphere on sphere type hip joint prosthesis.

Referring to the drawings, FIG. 1 shows a conventional sphere on sphere prosthetic hip joint. The joint consists of an acetabular cup 1 and a spherical head 2 of a femoral component having a bearing surface 4. The cup 1 includes a socket with a spherical concave surface 3. In the example illustrated, the radius $R_1$ of the head surface 4 is 14 mm and the radius $R_2$ of the cup surface 3 is 14.2 mm, giving a difference of 0.2 mm. This difference affords a clearance 6 between the two components of the joint and lubricating fluid is able to penetrate between the two within this clearance.

When the joint is placed under load, initial contact between the two surfaces 3, 4 occurs at a point 5. As the load is increased, surface deformation will cause the contact area to spread until the elastic restoring forces are equal to the applied load.

Because the predominant movement of the natural hip joint is one of rotation about the femoral head, the two radii $R_1$ and $R_2$ are selected to be close to one another, thereby reducing to a minimum the amount of play in the joint. However, limitations on the accuracy with which spherical surfaces can be made means that a space between the bearing surfaces of a few micrometres must be introduced in order to prevent contact between the surfaces during articulation, leading to the joint becoming locked against further articulation.

Figure 2:
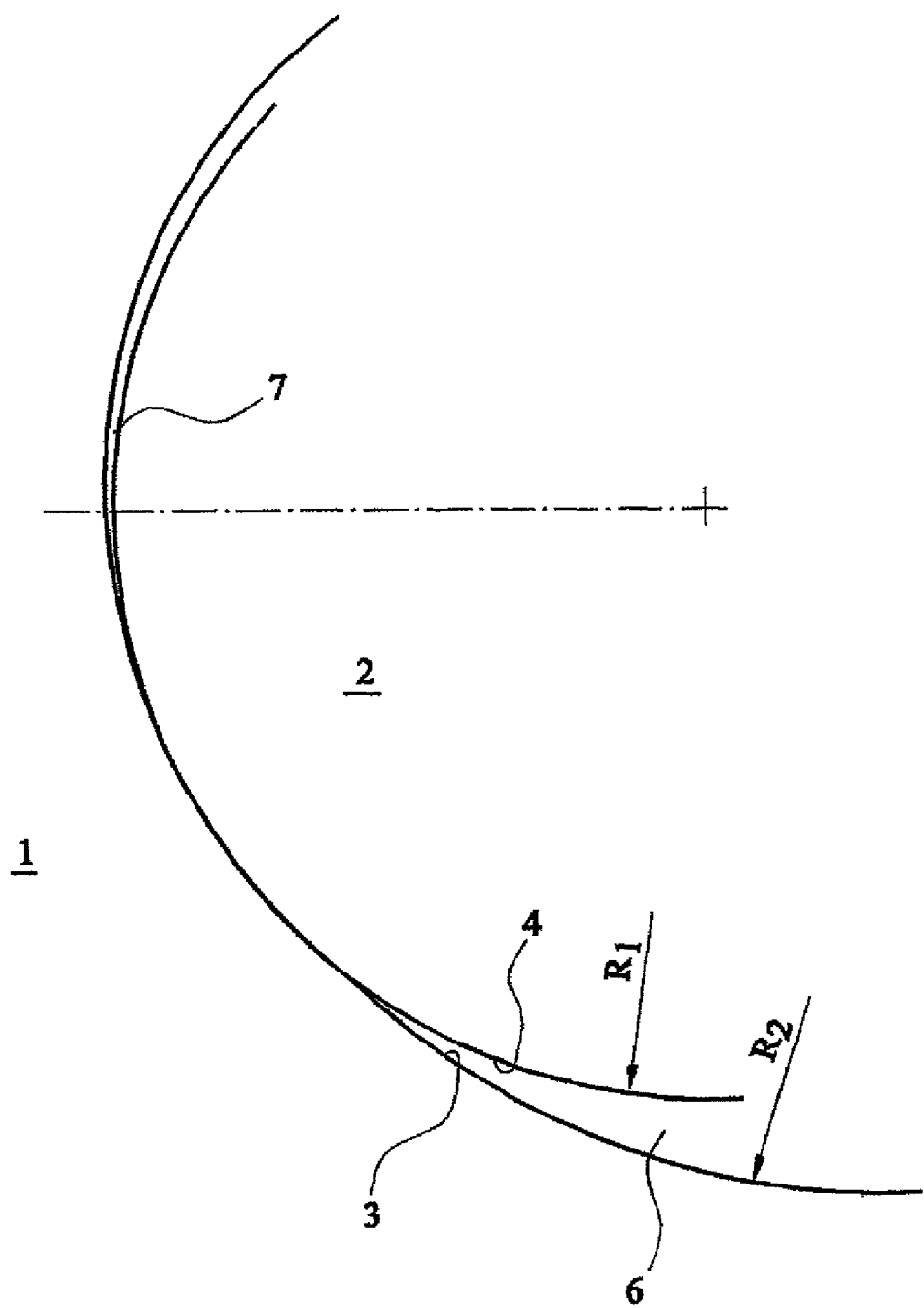
FIG. 2 illustrates a joint prosthesis of the kind known from WO-A-95/23566.

FIG. 2 illustrates joint construction which is known from WO-A-95/23566, which consists of an acetabular cup 1 and the spherical head 2 of a femoral component. In this joint, $R_1$ is greater than $R_2$. The surface of the spherical head is referenced 4. In this case, the surface 3 of the socket in the acetabular cup 1 has a geometry which allows the rate of change of the curvature of the surface to be varied continuously over the surface. A consequence of this geometry is that pools of lubricating fluid 7 are trapped in the contact region and they may accumulate debris resulting in increased wear.

Figure 3:
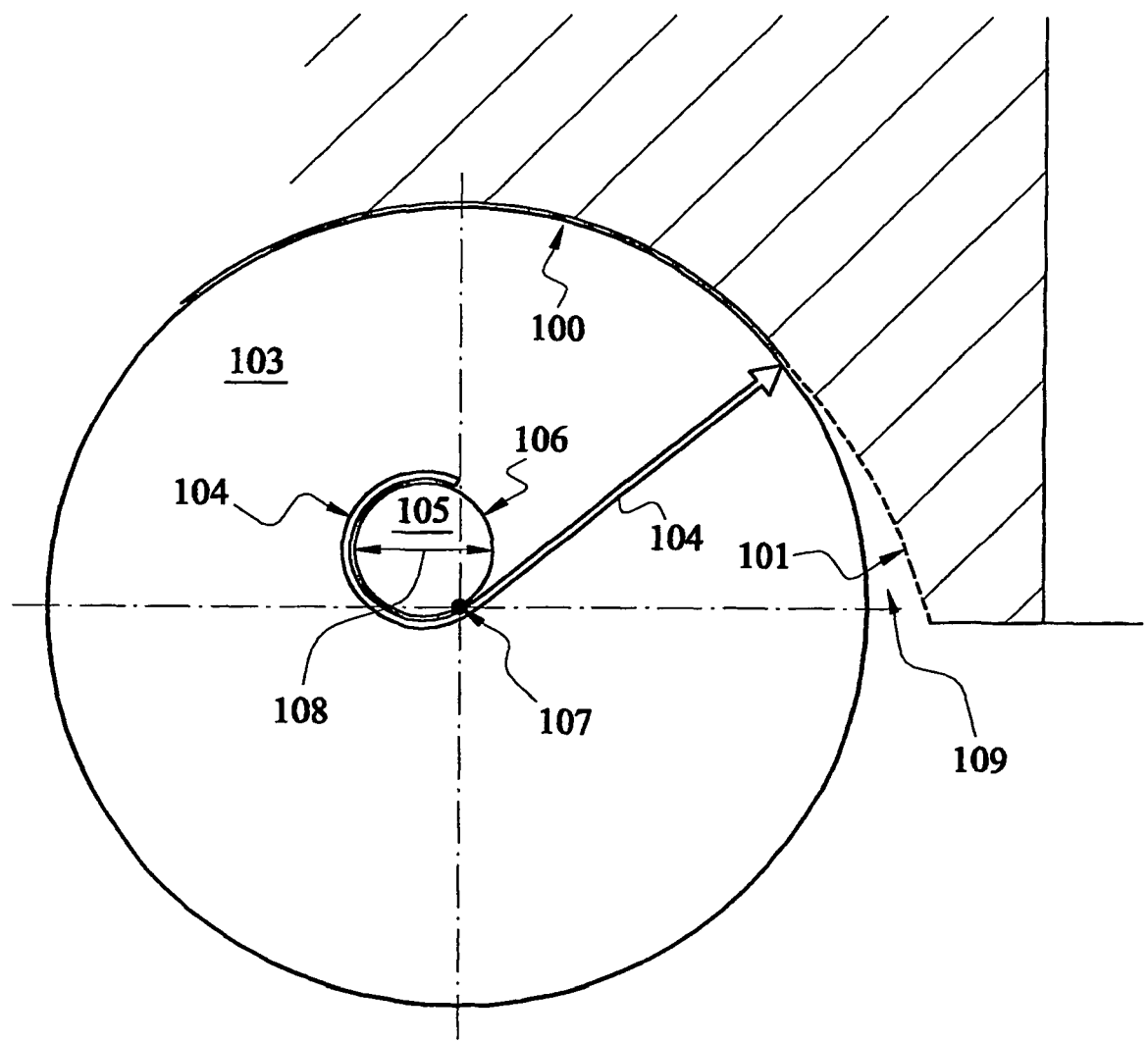
FIG. 3 illustrates a joint prosthesis according to the present invention.

FIG. 3 illustrates one embodiment of the present invention in which a stem component has a substantially spherical head 103, and the bearing surface of the socket in which the head fits has a spherical portion 100 which is transformed into a non-spherical portion 101. The non-spherical portion 101 has the configuration of a part of an involute. The involute can be regarded as being formed by a thread 104 unwinding from an imaginary bobbin 105 which is always positioned with its circumference 106 on the centre 107 of the sphere which defines the spherical portion 100. The diameter 108 of the bobbin 105 may be varied to vary the rate of divergence of the involute portion 101 from the spherical portion 100.

It can be seen from FIG. 3 that a gap 109 of increasing width opens between the head 103 of the stem component and the bearing surface 100, 101 of the socket. However, there is surface to surface contact between the bearing surfaces of the two components at and around the poles of the two components, even under zero load conditions.

The invention claimed is:

1. An orthopaedic joint prosthesis, comprising:
a generally rounded head portion with a rounded head bearing surface, the head bearing surface being symmetrical about a head axis and having a head pole; and
a cup configured to receive the head portion and to articulate with the head portion when the cup is assembled with the head portion, the cup having a rounded cup bearing surface, the cup bearing surface being symmetrical about a cup axis and having a cup pole;
wherein the cup bearing surface has a first cup bearing surface and a second cup bearing surface, the first cup bearing surface having a radius of curvature that continuously and monotonically decreases as the angle between the cup radius and the cup axis decreases in a direction towards the cup pole to a circumferential line, the first cup bearing surface being substantially linear or having substantially the shape of at least a part of a parabola, a hyperbola or an involute, when viewed in cross-section on the cup axis, the second cup bearing surface being that surface located between the circumferential line and the cup pole, the second cup bearing surface having a constant cup radius and a cup center defined by the constant cup radius;
the cup and the head portion being configured such that when the cup is assembled with the head portion and the cup axis of symmetry and the head axis of symmetry are aligned, the distance between the second cup bearing surface and the head bearing surface is substantially uniform.

2. The prosthesis of claim 1, wherein the head portion forms part of a femoral component of a hip joint prosthesis, and the cup is the acetabular component of a hip joint prosthesis.

3. The prosthesis of claim 1, wherein the bearing surface of at least one of the cup and head portion is formed of a metal.

4. The prosthesis of claim 1, wherein the angle formed between the cup radius and the cup axis at the circumferential line is not more than about 90 degrees.

5. The prosthesis of claim 1, wherein the circumferential line subtends an angle at the cup center of at least about 20 degrees.

6. The prosthesis of claim 1, wherein the head portion has a portion defined by a constant radius.

7. The prosthesis of claim 1, wherein the head radius increases continuously and monotonically until a head circumferential line, whereat the head radius is constant.

8. An orthopaedic joint prosthesis, comprising:
a generally rounded head portion with a rounded head bearing surface, the head bearing surface being symmetrical about a head axis and having a head pole; and
a cup configured to receive the head portion and to articulate with the head portion when the cup is assembled with the head portion, the cup having a rounded cup bearing surface, the cup bearing surface being symmetrical about a cup axis and having a cup pole;
wherein the head bearing surface has a first head bearing surface and a second head bearing surface, the first head bearing surface having a head radius of curvature that continuously and monotonically increases as the angle between the head radius and the head axis decreases in a direction towards the head pole to a circumferential line, the first head bearing surface having substantially the shape of at least a part of a parabola, a hyperbola or an involute, when viewed in cross-section on the head axis, the second head bearing surface being that surface located between the circumferential line and the head pole, the second head bearing surface having a constant head radius and a head center defined by the constant head radius;
the cup and the head portion being configured such that when the cup is assembled with the head portion and the cup axis of symmetry and the head axis of symmetry are aligned, the distance between the second head bearing surface and the cup bearing surface is substantially uniform.

9. The prosthesis of claim 8, wherein the head portion forms part of a femoral component of a hip joint prosthesis, and the cup is the acetabular component of a hip joint prosthesis.

10. The prosthesis of claim 8, wherein the bearing surface of at least one of the cup and head portion is formed of a metal.

11. The prosthesis of claim 8, wherein the angle formed between the head radius and the head axis at the circumferential line is not more than about 90 degrees.

12. The prosthesis of claim 8, wherein the circumferential line subtends an angle at the head center of at least about 20 degrees.

13. The prosthesis of claim 8, wherein the cup has a portion defined by a constant radius.

14. The prosthesis of claim 8, where the cup radius decreases continuously and monotonically until a cup circumferential line, whereat the cup radius is constant.

* * * * *